United States Patent
Franz et al.

(10) Patent No.: US 9,826,931 B2
(45) Date of Patent: Nov. 28, 2017

(54) MEDICAL WORKSTATION WITH INTEGRATED SUPPORT OF PROCESS STEPS

(71) Applicant: Dräger Medical GmbH, Lübeck (DE)

(72) Inventors: Frank Franz, Stockelsdorf (DE); Jürgen Manigel, Hamburg (DE); Michael Wilkening, Lübeck (DE); Wilfried Buschke, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 14/600,544

(22) Filed: Jan. 20, 2015

(65) Prior Publication Data

US 2015/0133797 A1 May 14, 2015

Related U.S. Application Data

(63) Continuation of application No. 12/493,503, filed on Jun. 29, 2009, now abandoned.

(30) Foreign Application Priority Data

Jul. 23, 2008 (DE) .................. 10 2008 034 234

(51) Int. Cl.
| | |
|---|---|
| A61B 5/00 | (2006.01) |
| A61M 16/00 | (2006.01) |
| A61M 21/00 | (2006.01) |
| G06F 19/00 | (2011.01) |
| A61B 5/0205 | (2006.01) |
| A61B 5/091 | (2006.01) |

(52) U.S. Cl.
CPC .......... *A61B 5/4821* (2013.01); *A61B 5/0205* (2013.01); *A61B 5/091* (2013.01); *G06F 19/3406* (2013.01); *G06F 19/3456* (2013.01)

(58) Field of Classification Search
None
See application file for complete search history.

(56) References Cited

U.S. PATENT DOCUMENTS

| | | | |
|---|---|---|---|
| 2002/0117174 A1* | 8/2002 | Colas .................. | 128/203.12 |
| 2008/0058612 A1* | 3/2008 | Ohyu .................. | G06Q 50/22 |
| | | | 600/300 |
| 2008/0086035 A1* | 4/2008 | Messerges et al. ......... | 600/300 |

FOREIGN PATENT DOCUMENTS

DE  10 2007 048 774 A1  5/2008

* cited by examiner

*Primary Examiner* — Christine H Matthews
*Assistant Examiner* — Shannon McBride
(74) *Attorney, Agent, or Firm* — McGlew and Tuttle, P.C.

(57) ABSTRACT

A device (13) is provided for use with a treatment device for treating a patient. The device (13) includes a detection device (17) for detecting at least one transition of the patient's treatment from a first phase of treatment to a second phase of treatment. A signal device (25) for sending at least one signal when the transition is detected. It proposes, furthermore, a workstation equipped herewith.

20 Claims, 4 Drawing Sheets

MEDICAL WORKSTATION WITH INTEGRATED SUPPORT OF PROCESS STEPS

CROSS REFERENCE TO RELATED APPLICATIONS

This application is a continuation under 37 CFR 1.53(b) of pending prior U.S. patent application Ser. No. 12/493,503 filed Jun. 29, 2009, which claims the priority of German Patent Application DE 10 2008 034 234.3 filed Jul. 23, 2008, the entire contents of each application are incorporated herein by reference.

FIELD OF THE INVENTION

The present invention pertains to a device for use with a treatment device for treating a patient pertains as well as to a workstation with a plurality of treating devices and/or monitoring devices for the treatment and/or monitoring of the patient.

BACKGROUND OF THE INVENTION

Modern workstations for the treatment of patients, for example, in the area of anesthesia, intensive care or neonatology, are known from practice. These workstations are characterized by high requirements imposed on the integration of devices used simultaneously or with one another. Thus, a number of devices, such as patient monitors, drug pumps, documentation systems and others are regularly connected functionally into one integrated workstation.

The treatment carried out with the workstation may comprise a plurality of phases, which follow each other and can often be clearly distinguished from one another. Based on the example of anesthesia, these phases may comprise induction of anesthesia, maintenance of anesthesia and emergence from anesthesia. These phases can, furthermore, be divided into detailed process steps. Additional activities, which pertain, for example, to the transfer of the patient from the induction room into the operating room, use of a heart-lung machine, taking of x-rays and the like, can be optionally added to the individual phases.

When passing over from a first phase of the treatment to a second phase, it is necessary, as a rule, to manually adapt a number of settings at the workstation or at the treatment devices comprised by said workstation to phase-typical or phase-dependent boundary conditions. Based on the example of anesthesia, interactions, such as changes in therapy settings (gas concentration, ventilation parameters), alarm settings (setting of alarm limits, activation/deactivation of alarms) as well as adjustments to the control surface, may be necessary at the time of such a phase transition. These actions, which are repeated during each treatment or anesthesia, must be carried out separately at individual components and devices comprised by the workstation.

The adjustments of the above-mentioned settings regularly represent a great effort for the person in charge of the treatment of the patient (the attending physician or nurse). It can therefore be observed in practice that regularly only the most needed adjustments, e.g., the control of the depth of anesthesia by setting the gaseous anesthetic concentration, are carried out at the time of transition from one phase of treatment to the next, especially under time pressure and stress. Other adjustments, for example, the adjustment of the alarm settings, are often neglected because of the complicated and uncomfortable operation. This may lead to undesired behavior of the device. One example of this is false alarms caused by suboptimal settings. However, dangerous situations may occur as well, because important interactions, such as reactivation of the alarms of hemodynamic monitoring after the termination of the operation of the heart-lung machine, were forgotten or were not executed for other reasons. Thus, the insufficient technical support does not prevent erroneous human behavior, which represents a considerable safety risk. Furthermore, the operation of the therapeutic workstation differs from one user to the next while the activities are comparable per se. This makes it difficult to improve quality by means of standardized procedures.

SUMMARY OF THE INVENTION

The object of the present invention is therefore to provide an improved device for supporting the user in charge of treating the patient.

According to the invention, a device is provided for use with a treatment device for treating a patient. The device comprises a detection means for detecting at least one phase of treatment and/or a transition of the patient's treatment from a first phase of treatment to a second phase of treatment and a signal means for sending at least one signal related to the detected phase of treatment and/or a signal when the transition is detected.

A device is provided according to the present invention, which has at least one detection means, by means of which a transition of the treatment of the patient from a first phase of treatment to a second phase of treatment, from a second phase of treatment to a third, from a third phase of treatment to a fourth, etc., can be detected. Moreover, a phase of treatment may also be able to be detected by means of the detection means. It is thus possible to detect or identify the first, present phase as such independently from a phase transition. Means known to the person skilled in the art, such as measuring means or patient monitors, may be used for this. Inputs by the user and combined, semiautomatic detections are likewise covered by the present invention.

A treatment phase is defined according to the present invention as a phase such as the phases of induction, anesthesia maintenance and wake-up phase mentioned above based on the example of anesthesia. Phases may comprise, according to the invention, a process or a plurality of processes as well as subphases. A phase is characterized by one parameter or a plurality of parameters. The transition from a first phase of treatment to a second one may therefore comprise a change in one or more parameters. A phase transition shall not be defined according to the present invention as being limited to intermittent transitions. A phase transition may rather also take place continuously, steadily, with a range of overlap or the like. It may therefore likewise be possible that both features of the first phase and features of the second phase can be observed simultaneously along with each other at defined times during the phase transition.

The device according to the present invention has, furthermore, at least one signal means for sending at least one signal as a consequence of the detection of a transition. A signal is defined according to the present invention quite generally as communicated information: The signal may indicate, for example, that a phase transition has taken place, is taking place or will take place (announcement). Besides or as an alternative to the communication function, the signal may also have a regulating or controlling action: Thus, the signal can inform the treating person of a phase transition in case of a suitable display (optical, acoustic, etc.). However, the signal may also act on the treatment device in such a way as to bring about, triggered by the reception of the signal, changes in treatment parameters and/or treatment processes. The signal, which is sent when the transition is detected, may precede the point in time at which the transition takes place, coincide with it or follow it in time. However, the signal may also pertain to a currently present phase only, i.e., it may be sent separated from a phase transition.

A phase or a phase transition can be detected according to the present invention by means of the detection means, for example, on the basis of a manual identification, e.g., by inputting via user interaction elements by the user. However, semiautomatic detection in the sense of identification, for example, by the analysis of information of the device sensors, of patient monitoring, of time measurement and the like is also defined according to the present invention as "detection," and so is an acknowledgement of a changeover from one phase to another, which is proposed by the user. Furthermore, purely automatic detection or identification of a phase or of a phase transition is also possible by means of the detection means. For example, the first-time recognition by the machine of an administration of anesthetics or the like can thus represent a phase transition. The sending of the signal may lead to automatic activation of the relevant alarm for the drug concentration.

Thus, a device with a display means for displaying the phase of treatment in which the patient is at a defined point in time is proposed in a preferred embodiment. This point in time may already be in the past, or it may pertain to the current point in time of polling or to a point in time in the future. The history of the treatment as well as expected treatment events such as phase transitions can thus be displayed by means of the display means. The knowledge of the treatment phase in which the patient is at the given point in time (displayed, for example, by the display means) makes it possible for the treating person to make a comparatively simple classification or rating of parameter values. Thus, a defined parameter value may be unusual for a first phase of treatment but usual for a second phase of treatment. If the phase of treatment of the patient during which the parameter had a defined parameter value is displayed to the treating person, deviations of the parameter can be determined more easily and countermeasures can possibly be initiated sooner.

In another preferred embodiment, the device according to the present invention has a selection means for selecting future treatment phases. The definition of "selection" also includes dropping, terminating, confirming and the like. The possible phases of treatment may be limited only to the phases that are meaningfully considered in the phase as the next phase based on a current phase. A selection of decisions can thus be offered to the treating person, in which every one of the options to be selected is also meaningful and desirable at the moment of selection. The mental selection of phases that are logically not possible or are less desirable in the particular case or at the particular moment is thus simplified. Nonsensical options can already be recognized as such at the device and cannot be offered in the first phase at all. Whether the selection takes place for the point in time of the selection operation or for a point in time that is in the future, especially the near future in time, makes no difference according to the present invention. The selection by means of the selection means may take place, for example, via one or more user interaction elements.

In yet another preferred embodiment according to the present invention, the device has a display means for displaying the actions associated with a phase or with a phase transition. A review of all the processes and operations that are relevant or necessary during the phase or at the time of the change from one phase to another may now be displayed to the user. This is especially helpful for those whose adjustment must not be overlooked and/or for those that are executed automatically by the treating person during the phase transition. The treating person is thus always in the picture about which changes are, in particular, associated or must be associated with a transition of the treatment from a first phase of treatment to a second one.

As was already provided in another preferred embodiment, individual actions or adjustment of the parameters thereof can be dropped by means of an input means. Furthermore, the phase transition can be confirmed or terminated.

In yet another preferred embodiment according to the present invention, the device has a data bank means for storing work flows, e.g., SOPs (Standard Operating Procedures) in a comprehensive manner. All the possibly parametrized actions and SOPs, which are carried out at the time of a phase transition or a transition from one state to another, can be defined in such a work flow data bank. For example, all ECG (electrocardiogram) alarms can be switched off or suspended following activation of the heart-lung machine. The data bank may contain meaningful presettings provided by the manufacturer, which can counteract erroneous setting and contribute to increased safety. The data bank may be designed such that it can be adjusted by the user to any desired standards, including local ones (SOPs) and norms with suitable tools. Whether or not a confirmation by the user is necessary before the action is carried out may possibly also be stored in the data bank. For example, it would be possible to specify that a message is sent to the operating room cleaning team without checking at the time of transition into the phase of emergence from an anesthesia. Besides the definition of a standard setting, the data bank may also have sets of settings, which are specific of certain interventions.

In yet another preferred embodiment, the device according to the present invention has, furthermore, a control means for controlling the work flow. Inputs entered via the selection means, the input means and the like as well as the detection means can be checked for consistency by means of such a control means. Furthermore, especially if the nature of the intervention or treatment can be polled from the surgery planning or other IT systems, the standard settings can be replaced with specific settings from the process data bank. Furthermore, the corresponding actions can be polled from the work flow data bank in case of phase transitions or transitions from one state to another and the actions stored may possibly be presented to the user for confirmation via the operating and display unit. The actions confirmed by the user can be communicated in suitable formats to receivers, for example, the internal device control or external IT systems.

The advantages that can be obtained according to the present invention comprise, among other things, optimal support of the person treating the patient and a general improvement in operating convenience.

Furthermore, the patient's safety is markedly increased compared to the extent hitherto common in practice. Improved safety of the patient and checking by the user, among other things, by the acknowledgment mechanism described, can thus be guaranteed. The number of human interactions necessary during a phase transition can be limited to a minimum. Operating convenience is increased while the probability of operating errors is minimized at the same time.

Furthermore, a positive effect on quality and efficiency can be achieved due to more standardized procedures (SOPs—Standard Operating Procedures) by means of the technical support of the treating person by the device according to the present invention. The present invention advantageously contributes, furthermore, to documentation, for example, in connection with surgical procedures, because phase transitions are already detected by the device and their occurrence only needs to be stored. This also applies to the processes brought about by the signal sent or to transmitted information. Furthermore, SOPs can be technically supported. Standardization and hence quality assurance of anesthesia can likewise be promoted. Higher-level work flows of the hospital can be triggered or supported by connecting external IT systems. A work flow data bank that can be freely configured offers the needed flexibility to add, adjust or update standards. The workstation documentation and especially the anesthesia documentation can be automatically complemented with information on the phase identification.

The present invention is also accomplished by a workstation, especially an anesthesia workstation, with a plurality of treatment devices and/or monitoring devices for treating and/or monitoring the patient with the device features for treatment phase detection and signaling. The workstation has at least one device according to the present invention as described above. Since all the advantages discussed above can be gained in full measure by means of the workstation according to the present invention, reference is expressly made here to the above discussion of these advantages to avoid repetitions.

The above-described procedure can also be applied in this form to other workstations, especially workstations used in emergency medicine. It is advantageous in this connection if a component of the integrated workstation ensures the needed connectivity and a computing unit images the above-described process logic.

It is advantageously possible in an intensive care workstation to adjust the settings of the actuator mechanism and alarm management as well as of the graphic user interface of the patient monitor, respirator, thermotherapy device, syringe/infusion pumps and hemofiltration apparatus during defined phases. These phases, which are associated with treatment steps performed at the patient, include, for example, basic nursing (washing, positioning), physical therapy, endotracheal suction, taking of blood, resuscitation, transport, etc.

What was said in connection with the intensive care workstation in reference to the above-described invention applies to the neonatological workstation. However, integration of thermotherapy (incubators, heat radiators) and the work flows associated therewith is of particular importance here.

The present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
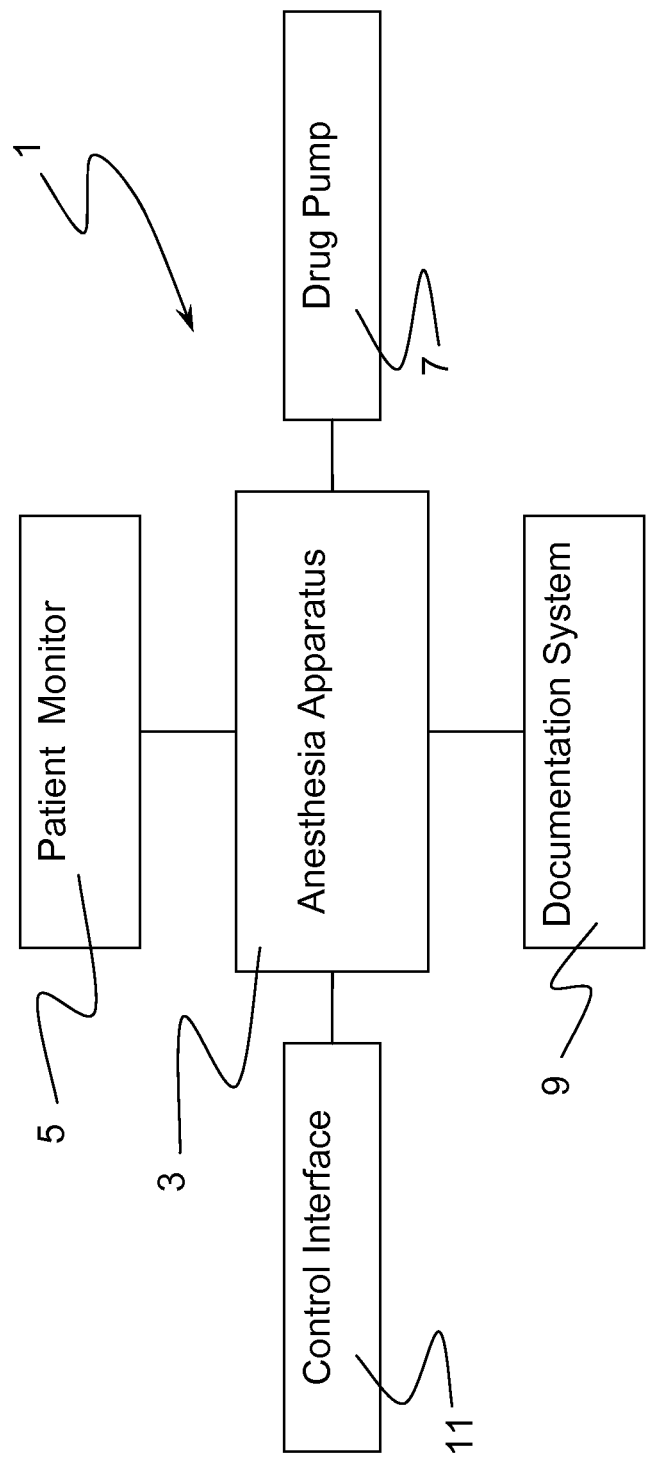
FIG. 1 is an example of an integrated anesthesia workstation.

Referring to the drawings in particular, FIG. 1 shows an example of an integrated workstation 1 for treating a patient from anesthesia. The anesthesia apparatus 3 as the core of the workstation 1 is technically linked with additional devices such as a patient monitor 5, drug pumps 7, a documentation system 9, a control interface 11 and other components.

Figure 2:
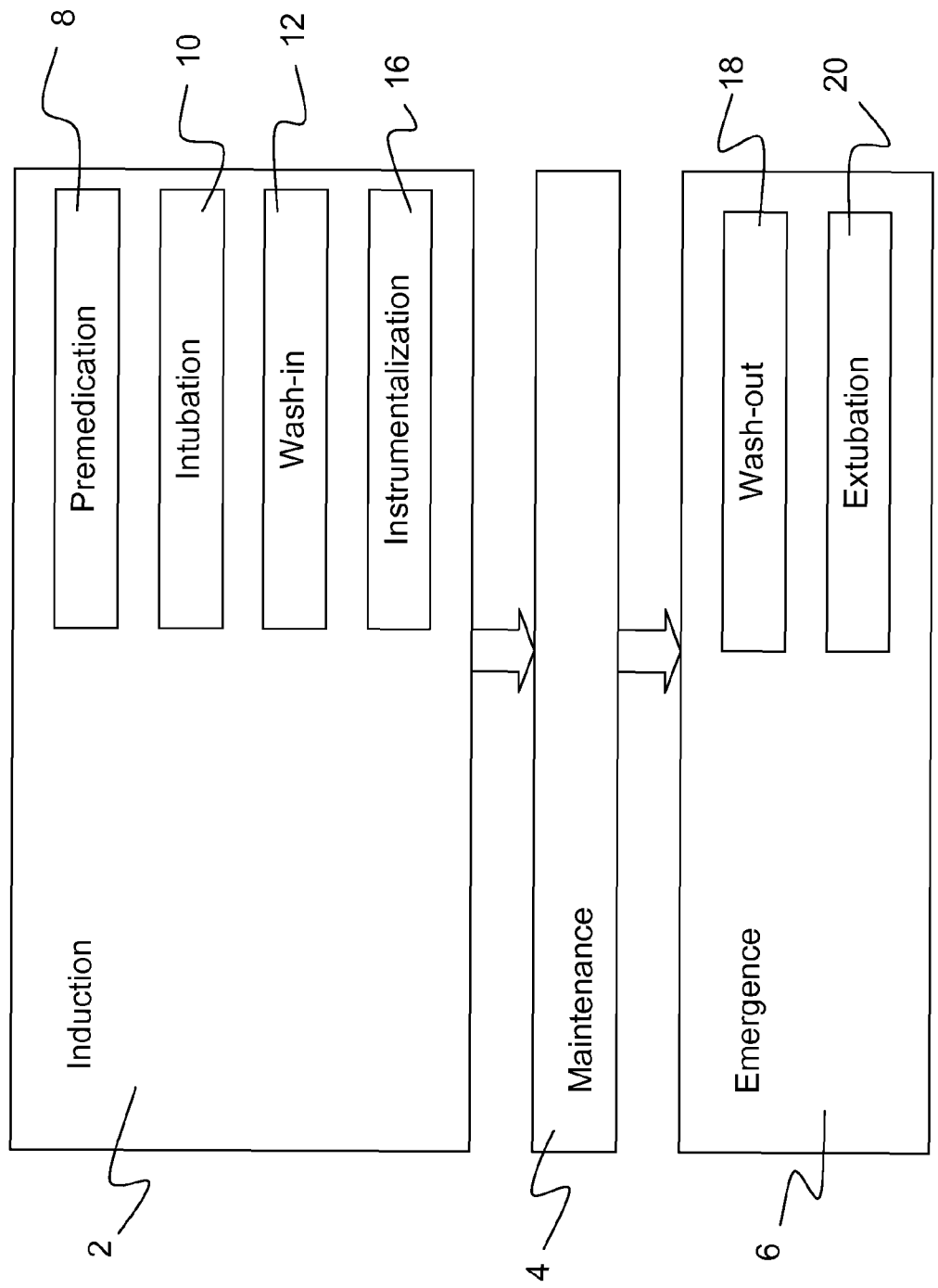
FIG. 2 is consecutive phases with respective phase transitions between them based on the example of anesthesia with a gaseous anesthetic.

FIG. 2 shows an example of consecutive phases of an anesthesia with a phase transition each between them. The phases "induction" 2, "maintenance" 4 and "emergence" 6 can be further divided into more detailed process steps such as "premedication" 8, "intubation" 10, "wash-in" 12, "instrumentalization" 16, "wash-out" 18 and "extubation" 20. They may optionally also be complemented with processes such as transfer of the patient from one operating room into another, the switching on of a heart-lung machine (HLM) 14, FIG. 3, and the like.

Figure 3:
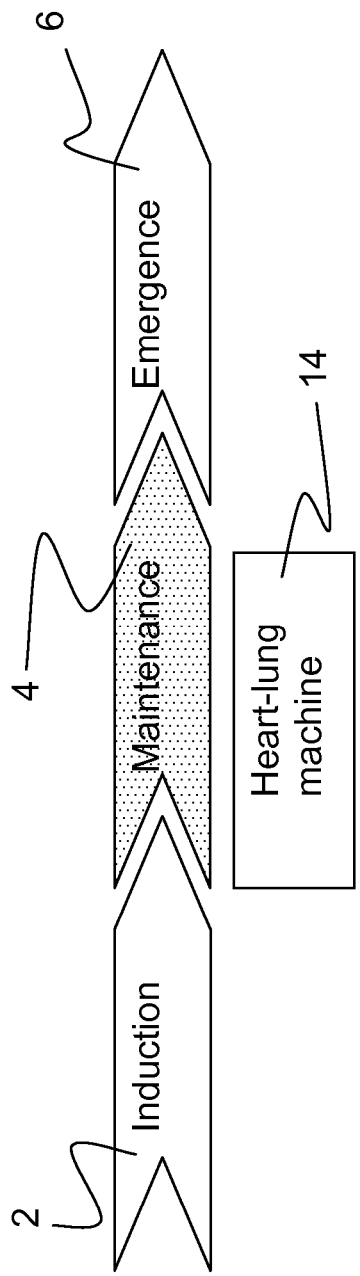
FIG. 3 is an example of a "phase indicator and phase transition" interface.

FIG. 3 shows an example of a "phase indicator and phase transition" interface. User interaction elements for the transition into another phase are displayed. Only logically possible phases, such as "induction" 2, "maintenance" 4 and use of the heart-lung machine 14 (HLM) and "emergence" 6, are displayed to the user for selection.

Figure 4:
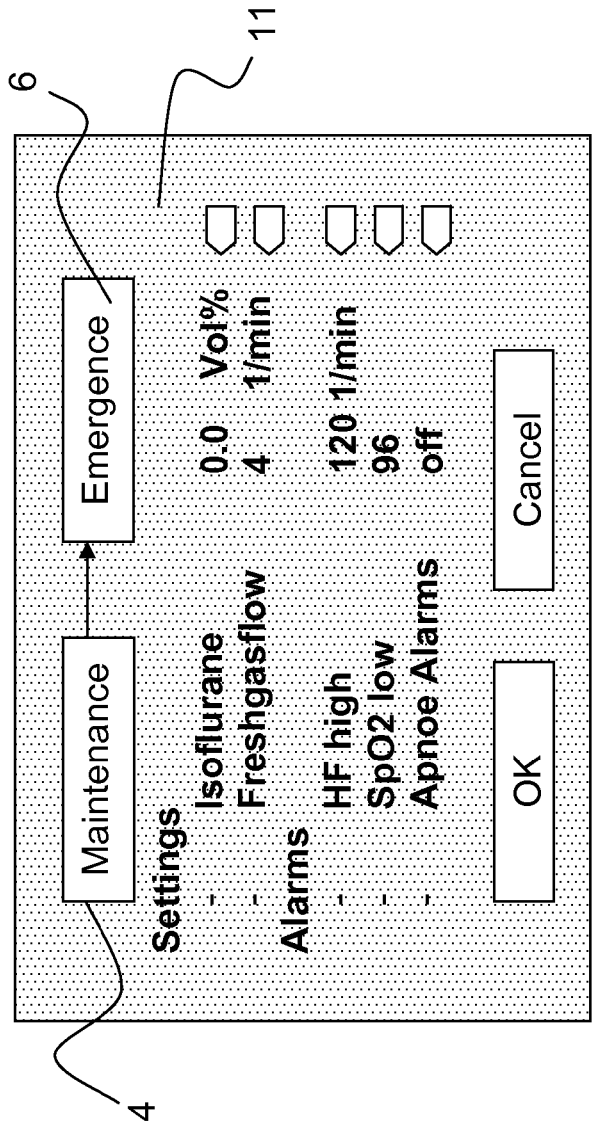
FIG. 4 is an example of a "Confirmation of phase transition" control interface.

FIG. 4 shows an example of a "confirmation of phase transition", "maintenance" 4, "emergence" 6 control interface 11 with a sequential succession of the relevant phases during anesthesia during a cardiac surgical intervention with the use of the heart-lung machine HLM, which [interface] can be used during a treatment according to the example shown in Table 1 with ten phase transitions ("0" to "9," see tabular representation in Table 1). The information that is displayed to the user during the particular phase transition for confirmation (cf. FIG. 4) is found under "therapy settings" and "alarm settings" in Table 1. Furthermore, the particular adjustments that are performed at the user interface are listed under "UI adjustments" (UI=User Interface). The communication of confirmed phase transitions with external IT systems for the purpose of documentation and process control is not shown or indicated in Table 1.

TABLE 1

| Phase | Phase transition | Therapy settings | Alarm settings | Control interface |
| --- | --- | --- | --- | --- |
| 0 | Standby → preoxygenation | Gas concentration: Oxygen douche | Alarms switched off | Display "Intubation;" display relevant |

TABLE 1-continued

| Phase | Phase transition | Therapy settings | Alarm settings | Control interface |
|---|---|---|---|---|
|  |  | Ventilation: manual/spontaneous Drugs: propofol & fentanyl + propofol bolus |  | parameters only |
| 1 | Preoxygenation → intubation | Gas concentration: Oxygen douche Ventilation: manual/spontaneous | Alarms switched off | Display: "Wash-in," capnogram analysis |
| 2 | Intubation → "Wash-in" | Gas concentration: 30% $O_2$/ 70% $N_2O$ Ventilation: automatic Drugs: " Stop propofol. sevoflurane 2%, during expiration | Ventilation alarms and hemodynamic alarms in Auto Wake-up mode | Display: "Instrumentalization" |
| 3 | "Wash-in" → instrumentalization |  | Hemodynamic alarms in Auto Wake-up mode | Display: "Maintenance" |
| 4 | Instrumentalization → maintenance |  | All alarms activated | Display: "HLM" Display: "Wash-out" |
| 5 | Maintenance → HLM | Ventilation: Pause/Off or manual/spontaneous or automatic ventilation | Reduced alarms, HLM mode | Display: "Maintenance" |
| 6 | HLM → Maintenance | Gas concentration: 30% $O_2$/ 70% $N_2O$ Ventilation: automatic Drugs: fentanyl and sevoflurane 2%, during expiration | All alarms activated | Display: "HLM" Display: "Wash-out" |
| 7 | Maintenance → Wash-out | Gas concentration: 100% $O_2$ Ventilation: automatic Drugs: none | Reduced alarms | Display: "Extubation" |
| 8 | "Wash-out" → extubation | Gas concentration: 100% $O_2$ Ventilation: automatic Drugs: none | Alarms switched off | Display: "Standby" |
| 9 | Extubation → standby | None | Alarms switched off |  |

A first phase transition is designated by "0" in Table 1. The user now administers an "oxygen douche" (100% $O_2$ with high fresh gas flow) to the patient for the first time and administers relaxing and sedating drugs in order to prepare the patient for intubation.

An "intubation" phase transition designated by "1" is confirmed by the user. He can very easily check the success of the intubation by means of the automatically displayed capnogram without being distracted by disturbing alarms; these are automatically suppressed, as can be seen in the "alarm settings" column.

The dialog for the wash-in is automatically offered to the user after intubation during the phase transition designated by "2" (capnogram analysis). Respiration and anesthesia with a gaseous anesthetic is started after confirmation of the values proposed by the treating person. Alarms that are no longer needed are in turn switched off.

If the expiratory target concentration in the breathing gas is reached, the dialog for a transition "3" into the phase of instrumentalization appears, during which all hemodynamic alarms are in the automatic wake-up mode after confirmation by the user.

If the induction measures are concluded, the user can change over manually into anesthesia maintenance (transition "4") by actuating the "maintenance" button. The patient is adequately respirated and anesthetized and all alarms are activated now.

The HLM is used (transition "5") in the course of surgery. The user actuates the "HLM" button for this purpose and confirms the corresponding dialog. The alarms are set to the HLM mode in order to avoid false alarms. Respiration and anesthesia are likewise reduced, because these tasks are taken over by the HLM.

If the output of the HLM is reduced in the further course, this can be detected from pulses of the invasive pressure and resumption of the ECG activity (transition "6"). This leads to automatic display of the corresponding dialog; respiration, dispensing of anesthetic and full alarm functionality are reactivated.

After conclusion of the procedure (transition "7"), the user can start the emergence from the anesthesia by actuating the "wash-out" button—the gaseous anesthetics are washed out, oxygen saturation is reached, and the alarm functionality is reduced.

If the patient is sufficiently alert (transition "8"), the user can prepare the patient for the extubation by actuating the "extubation" button. All alarms are deactivated for this.

The anesthesia is thus concluded and the apparatus can pass over into the standby mode (transition "9").

Figure 5:
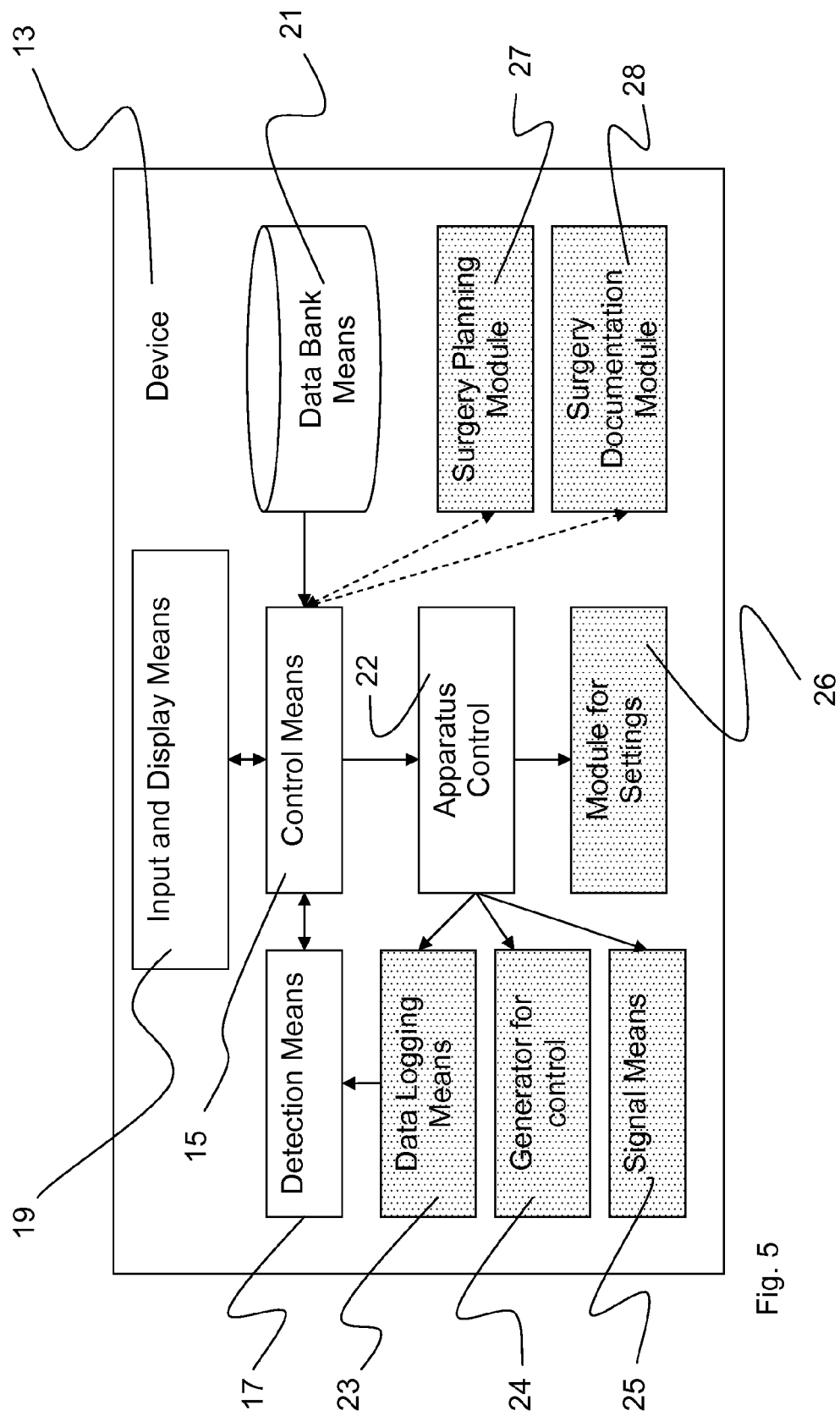
FIG. 5 is a possible system setup for a device according to the present invention.

FIG. 5 shows possible components of a device 13 according to the present invention with a control means 15 for work flows, with a detection means 17, with an input and display means 19, with a data bank means 21 and with additional means. It is pointed out that individual components may be provided in order to assume more than only one function. For example, one means may send a signal and also store same.

The control means 15 is connected via an apparatus control 22 to a data logging means 23, to a generator 24 for generating control surfaces and to a signal means 25. Settings may be made via a module 26. Furthermore, a surgery planning module 27 and a surgery documentation module 28 are provided.

While specific embodiments of the invention have been shown and described in detail to illustrate the application of the principles of the invention, it will be understood that the invention may be embodied otherwise without departing from such principles.

What is claimed is:

1. A method for monitoring different phases of an anesthesia machine, the method comprising:
providing an anesthesia device;
providing a plurality of anesthesia phases of treatment with said anesthesia device, said plurality of anesthesia phases of treatment comprising an induction phase, a maintenance phase and an emergence phase;
providing a detection means;
providing a display means comprising a user interface;
determining a current anesthesia phase of treatment of the patient with said detection means;
displaying the current anesthesia phase of treatment on said display means;
detecting at least one transition from said current anesthesia phase of treatment to a next anesthesia phase of treatment;
displaying actions associated with one or more of said current anesthesia phase of treatment and said at least one transition from said current anesthesia phase of treatment to said next anesthesia phase of treatment on said display means, said actions corresponding to processes and operations associated with said current anesthesia phase of treatment and/or said at least one transition from said current anesthesia phase of treatment to said next anesthesia phase of treatment, wherein parameters of said processes and operations are displayed on said display means during one or more of said current anesthesia of treatment and said at least one transition from said current anesthesia phase of treatment;
adjusting one or more of said parameters on said display means; and
selecting at least one future anesthesia phase of treatment based on said actions displayed on said display means via said user interface, wherein said display means displays said selected at least one future anesthesia phase of treatment.

2. A method in accordance with claim 1, further comprising:
providing a signal means;
sending at least a signal when the at least one transition from said current anesthesia phase of treatment to said next anesthesia phase of treatment is detected via said signal means, wherein the at least one transition of one anesthesia phase to the next anesthesia phase is one of a transition from standby to preoxygenation, a transition from preoxygenation to intubation, a transition from intubation to a wash-in process, a transition from a wash-in process to instrumentalization, a transition from instrumentalization to maintenance, a transition from maintenance to heart-lung-machine-mode, a transition from heart-lung-machine-mode to maintenance, a transition from maintenance to a wash-out process, a transition from a wash-out process to extubation and a transition from extubation to standby, said parameters corresponding to one or more of gas concentration parameters, alarm parameters and ventilation parameters.

3. A method in accordance with claim 1, further comprising:
providing a data bank means; and
storing work flows data with said data bank means.

4. A method in accordance with claim 3, further comprising:
providing a control means; and
controlling said work flows data with said control means.

5. A method in accordance with claim 1, wherein another future phase of anesthesia treatment is selected based on said current anesthesia phase of treatment and/or said at least one transition from said current anesthesia phase of treatment to said next anesthesia phase of treatment, wherein said display means displays a transition from standby to preoxygenation, said display means displaying a transition from preoxygenation to intubation after displaying said transition from standby to preoxygenation, said display means displaying a transition from intubation to a wash-in process after displaying said transition from standby to preoxygenation and after displaying said transition from preoxygenation to intubation, said display means displaying a transition from a wash-in process to instrumentalization after displaying said transition from standby to preoxygenation and after displaying said transition from preoxygenation to intubation and after displaying said transition from intubation to said wash-in process, said display means displaying a transition from instrumentalization to maintenance after displaying said transition from standby to preoxygenation and after displaying said transition from preoxygenation to intubation and after displaying said transition from intubation to said wash-in process and after displaying said transition from said wash-in process to instrumentalization, said display means displaying a transition from maintenance to heart-lung-machine-mode after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance, said display means displaying a transition from heart-lung-machine-mode to maintenance after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode, said display means displaying a transition from maintenance to a wash-out process after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance, said display means displaying a transition from a wash-out process to extubation after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance and after displaying said transition from maintenance to said wash-out process, said display means displaying a transition from extubation to standby after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance and after displaying said transition from maintenance to said wash-out process and after displaying said transition from said wash-out process to extubation.

6. A method in accordance with claim 5, wherein one or more of said preoxygenation, said intubation, said wash-in process and said instrumentalization is detected when said at least one anesthesia phase of said plurality of anesthesia phases is said induction phase, wherein said display means displays said actions when said display means displays said transition from standby to preoxygenation, said display means displaying said actions when said display means displays said transition from preoxygenation to intubation, said display means displaying said actions when said display means displays said transition from intubation to said wash-in process, said display means displaying said actions when said display means displays said transition from said wash-in process to instrumentalization, said display means displaying said actions when said display means displays said transition from instrumentalization to maintenance, said display means displaying said actions when said display means displays said transition from maintenance to heart-lung-machine-mode, said display means displaying said actions when said display means displays said transition from heart-lung-machine-mode to maintenance, said display means displaying said actions when said display means displays said transition from maintenance to said wash-out process, said display means displaying said actions when said display means displays said transition from said wash-out process to extubation, said display means displaying said actions when said display means displays said transition from extubation to standby.

7. A method in accordance with claim 5, wherein one or more of said wash-out process and said extubation is detected when said at least one of said plurality of anesthesia phases is said emergence phase.

8. A method in accordance with claim 1, wherein said display means comprises a phase indicator and phase transition interface, said phase indicator and phase transition interface displaying said current anesthesia phase of treatment and/or said transition from said current anesthesia phase of treatment to said next anesthesia phase of treatment.

9. A method, comprising:
providing an anesthesia apparatus;
providing a patient with a plurality of anesthesia treatment phases with said anesthesia apparatus, said plurality of anesthesia treatment phases comprising an induction phase of anesthesia, a maintenance phase of anesthesia and an emergence phase of anesthesia; and
determining at least one transition of a treatment of the patient from one of said anesthesia treatment phases to another one of said anesthesia treatment phases, wherein the at least one transition from one of said anesthesia phases to said another one of said anesthesia phases is one of a transition from standby to preoxygenation, a transition from preoxygenation to intubation, a transition from intubation to a wash-in process, a transition from a wash-in process to instrumentalization, a transition from instrumentalization to maintenance, a transition from maintenance to heart-lung-machine-mode, a transition from heart-lung-machine-mode to maintenance, a transition from maintenance to a wash-out process, a transition from a wash-out process to extubation and a transition from extubation to standby;
providing a display means;
displaying said at least one transition from said one of said anesthesia phases to said another one of said anesthesia phases on said display means;
displaying at least actions associated with said at least one transition from one of said anesthesia treatment phases to another one of said anesthesia treatment phases on said display means, said actions corresponding to processes and operations associated with at least said at least one transition of the treatment of the patient from said one of said anesthesia phases of treatment to said another one of said anesthesia phases of treatment;
displaying parameters associated with said processes and operations on said display means during said at least one transition from said one of said anesthesia phases to said another one of said anesthesia phases;
adjusting one or more of said parameters on said display means during said at least one transition from one of said anesthesia treatment phases to another one of said anesthesia treatment phases to provide one or more adjusted parameters, said one or more adjusted parameters being displayed on said display means;
selecting at least one future phase of anesthesia treatment based on said actions displayed on said display means.

10. A method in accordance with claim 9, further comprising:
sending at least a signal when the at least one transition is detected; and
operating said anesthesia apparatus based on said at least one selected future phase of anesthesia treatment, said parameters corresponding to one or more of gas concentration parameters, alarm parameters and ventilation parameters.

11. A method in accordance with claim 10, wherein said induction phase comprises said preoxygenation, said intubation, said wash-in process and said instrumentalization, said emergence phase comprising said wash-out process and said extubation, said display means comprising a phase indicator and phase transition interface, said phase indicator and phase transition interface displaying said at least one transition of the treatment of the patient from said one of said anesthesia phases of treatment to said another one of said anesthesia phases of treatment, said anesthesia treatment phases comprising one or more future phases of anesthesia treatment, wherein said one or more said future phases of anesthesia treatment is selected based on at least said at least one transition of the treatment of the patient from said one of said anesthesia treatment phases to said another one of said anesthesia treatment phases, said one or more said future phases of anesthesia treatment being displayed on said display means.

12. A method in accordance with claim 10, wherein one or more of said preoxygenation, said intubation, said wash-in process and said instrumentalization is detected when said at least one of said plurality of anesthesia phases is said induction phase, wherein one or more of said wash-out process and said extubation is detected when at least one of said plurality of anesthesia phases is said emergence phase.

13. A method in accordance with claim 9, further comprising:
  storing work flows data in a data bank means, wherein said display means displays a transition from standby to preoxygenation, said display means displaying a transition from preoxygenation to intubation after displaying said transition from standby to preoxygenation, said display means displaying a transition from intubation to a wash-in process after displaying said transition from standby to preoxygenation and after displaying said transition from preoxygenation to intubation, said display means displaying a transition from awash-in process to instrumentalization after displaying said transition from standby to preoxygenation and after displaying said transition from preoxygenation to intubation and after displaying said transition from intubation to said wash-in process, said display means displaying a transition from instrumentalization to maintenance after displaying said transition from standby to preoxygenation and after displaying said transition from preoxygenation to intubation and after displaying said transition from intubation to said wash-in process and after displaying said transition from said wash-in process to instrumentalization, said display means displaying a transition from maintenance to heart-lung-machine-mode after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance, said display means displaying a transition from heart-lung-machine-mode to maintenance after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode, said display means displaying a transition from maintenance to a wash-out process after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from lea heart-lung-machine-mode to maintenance and after displaying said transition from maintenance to said wash-out process, said display means displaying a transition from extubation to standby after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance and after displaying said transition from maintenance to said wash-out process and after displaying said transition from said wash-out process to extubation.

14. A method in accordance with claim 13, further comprising:
  controlling said work flows data with a control means, wherein said display means displays said actions when said display means displays said transition from standby to preoxygenation, said display means displaying said actions when said display means displays said transition from preoxygenation to intubation, said display means displaying said actions when said display means displays said transition from intubation to said wash-in process, said display means displaying said actions when said display means displays said transition from said wash-in process to instrumentalization, said display means displaying said actions when said display means displays said transition from instrumentalization to maintenance, said display means displaying said actions when said display means displays said transition from maintenance to heart-lung-machine-mode, said display means displaying said actions when said display means displays said transition from heart-lung-machine-mode to maintenance, said display means displaying said actions when said display means displays said transition from maintenance to said wash-out process, said display means displaying said actions when said display means displays said transition from said wash-out process to extubation, said display means displaying said actions when said display means displays said transition from extubation to standby.

15. A method, comprising:
  providing an anesthesia device;
  treating a patient with a plurality of anesthesia phases of treatment, said plurality of anesthesia phases of treatment comprising an induction phase of anesthesia, a maintenance phase of anesthesia and an emergence phase of anesthesia;
  determining at least one transition from one phase of said anesthesia phases of treatment to a subsequent phase of said anesthesia phases of treatment, wherein said at least one transition from said one phase of said anesthesia phases of treatment to said subsequent phase of said anesthesia phases of treatment is one of a transition from standby to preoxygenation, a transition from preoxygenation to intubation, a transition from intubation to a wash-in process, a transition from a wash-in process to instrumentalization, a transition from instrumentalization to maintenance, a transition from maintenance to heart-lung-machine-mode, a transition from heart-lung-machine-mode to maintenance, a transition from maintenance to a wash-out process, a transition from a wash-out process to extubation and a transition from extubation to standby;

providing a display means comprising a user anesthesia phase selection interface;

displaying at least one of the phases of treatment in which the patient is at a point in time on said display means, displaying said transition from said one phase to said subsequent phase of said anesthesia phases of treatment on said display means, displaying actions associated with said transition from said one phase to said subsequent phase of said anesthesia phases of treatment on said display means and displaying parameters during said at least one transition from said one of said anesthesia phases of treatment to said subsequent phase of said anesthesia phases of treatment, said actions corresponding to processes and operations taking place during said at least one transition from said one of said anesthesia phases of treatment to said subsequent phase of said anesthesia phases of treatment, said parameters being associated with said processes and operations;

adjusting at least one of said parameters on said display means during said transition from said one phase to said subsequent phase of said anesthesia phases of treatment to provide at least one adjusted parameter, said at least one adjusted parameter being displayed on said display means; and selecting at least one future phase of anesthesia treatment based on said actions displayed on said display means via said user anesthesia phase selection interface.

16. A method in accordance with claim 15, further comprising:

sending a signal related to at least one detected phase of treatment and said at least one transition from said one phase of said anesthesia phases of treatment to said subsequent phase of said anesthesia phases of treatment, wherein said anesthesia device is operated based on said at least one selected future phase of anesthesia treatment, said parameters corresponding to one or more of gas concentration parameters, alarm parameters and ventilation parameters.

17. A method in accordance with claim 16, further comprising:

selecting a future phase of anesthesia based on said at least one of the phases of treatment in which the patient is at a point in time and said actions associated with a change from one phase to another.

18. A method in accordance with claim 17, wherein at least one transition from one phase of said anesthesia phases of treatment to a subsequent phase of said anesthesia phases of treatment is determined via one or more of a measuring device, a patient monitor and a semiautomatic detection device.

19. A method in accordance with claim 16, wherein said induction phase comprises said preoxygenation, said intubation, said wash-in process and said instrumentalization, said emergence phase comprising said wash-out process and said extubation, said display means comprising a phase indicator and phase transition interface, said phase indicator and phase transition interface displaying one or more of said at least one transition of the patient's treatment from said one of said anesthesia phases of treatment to said subsequent phase of said anesthesia phases of treatment, said possible phases of treatment comprising future anesthesia phases of treatment, wherein at least one of said future anesthesia phases of treatment is selected based at least on said at least one transition from one phase of said anesthesia phases of treatment to said subsequent phase of said anesthesia phases of treatment, wherein one or more of said preoxygenation, said intubation, said wash-in process and said instrumentalization is detected in said induction phase, wherein one or more of said wash-out process and said extubation is detected in said emergence phase.

20. A method in accordance with claim 15, wherein said display means displays said transition from standby to preoxygenation, said display means displaying said transition from preoxygenation to intubation after displaying said transition from standby to preoxygenation, said display means displaying said transition from intubation to said wash-in process after displaying said transition from standby to preoxygenation and after displaying said transition from preoxygenation to intubation, said display means displaying said transition from said wash-in process to instrumentalization after displaying said transition from standby to preoxygenation and after displaying said transition from preoxygenation to intubation and after displaying said transition from intubation to said wash-in process, said display means displaying said transition from instrumentalization to maintenance after displaying said transition from standby to preoxygenation and after displaying said transition from preoxygenation to intubation and after displaying said transition from intubation to said wash-in process and after displaying said transition from said wash-in process to instrumentalization, said display means displaying said transition from maintenance to heart-lung-machine-mode after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance, said display means displaying said transition from heart-lung-machine-mode to maintenance after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode, said display means displaying said transition from maintenance to a wash-out process after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance, said display means displaying said transition from a wash-out process to extubation after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance and after displaying said transition from maintenance to said wash-out process, said display means displaying said transition from extubation to standby after displaying said transition from standby to preoxygenation and after displaying said transition from preoxygenation to intubation and after displaying said transition from intubation to said wash-in process and after displaying said transition from said wash-in process to instrumentalization and after displaying said transition from instrumentalization to maintenance and after displaying said transition from maintenance to heart-lung-machine-mode and after displaying said transition from heart-lung-machine-mode to maintenance and after displaying said transition from maintenance to said wash-out process and after displaying said transition from said wash-out process to extubation, wherein said display means displays said actions when said display means displays said transition from standby to preoxygenation, said display means displaying said actions when said display means displays said transition from preoxygenation to intubation, said display means displaying said actions when said display means displays said transition from intubation to said wash-in process, said display means displaying said actions when said display means displays said transition from said wash-in process to instrumentalization, said display means displaying said actions when said display means displays said transition from instrumentalization to maintenance, said display means displaying said actions when said display means displays said transition from maintenance to heart-lung-machine-mode, said display means displaying said actions when said display means displays said transition from heart-lung-machine-mode to maintenance, said display means displaying said actions when said display means displays said transition from maintenance to said wash-out process, said display means displaying said actions when said display means displays said transition from said wash-out process to extubation, said display means displaying said actions when said display means displays said transition from extubation to standby.

\* \* \* \* \*